United States Patent

Giani et al.

[11] Patent Number: 4,983,620
[45] Date of Patent: Jan. 8, 1991

[54] PHARMACOLOGICALLY ACTIVE ALKYLTHIOBENZIMIDAZOLE DERIVATIVES AND PROCESS FOR THE PREPARATION THEREOF

[75] Inventors: Roberto P. Giani, Locate Triulzi; Ettore Parini, Cologno Monzese; Giancarlo Tonon, Milan, all of Italy

[73] Assignee: Dompé Farmaceutici S.p.A., Milan, Italy

[21] Appl. No.: 327,094

[22] Filed: Mar. 22, 1989

[30] Foreign Application Priority Data

Mar. 25, 1988 [IT] Italy ............................ 19958 A/88

[51] Int. Cl.$^5$ ................. A61K 31/415; A61K 31/535; C07D 235/28; C07D 413/12
[52] U.S. Cl. .................... 514/395; 514/234.5; 514/253; 514/322; 544/139; 544/370; 546/199; 548/326; 548/327; 548/329
[58] Field of Search .............. 548/326, 327, 329; 546/199; 544/139, 370; 514/395, 322, 253, 234.5

[56] References Cited

PUBLICATIONS

Chemical Abstracts, 80:108531q (1974) [Japan, Kokai, 74, 13,172, Hasegawa et al., 2/5/74].
Chemical Abstracts, 82:156308k (1975) [Japan, 74, 41,198, Hasegawa et al., 11/7/74].

Primary Examiner—Mary C. Lee
Assistant Examiner—Lenora Miltenberger
Attorney, Agent, or Firm—Stevens, Davis, Miller & Mosher

[57] ABSTRACT

New alkylthiobenzimidazole derivatives are described which belong to the class of formula:

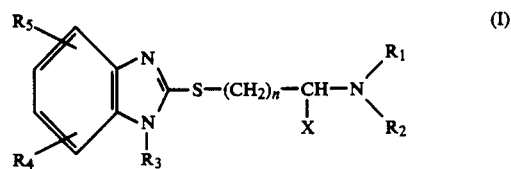

wherein
$R_1$ and $R_2$ each represent a 1–3 carbon atom alkyl radical or they may form with the adjacent nitrogen atom, an optionally substituted heterocyclic ring,
X represents a hydrogen atom or methyl radical
n is 1 or 2
$R_3$ represents a 4–6 carbon atom alkoxyalkyl radical, a 7 or 8 carbon atom arylalkyl radical or a 5 or 6 carbon atom cycloalkyl radical with the exception that $R_3$ may not be an arylalkyl radical when $R_1$ and $R_2$ each represent a 1–3 carbon atom alkyl radical
$R_4$ and $R_5$ may be the same or different and each represent a hydrogen atom or a 1–2 carbon atom alkyl or they, attached at the positions 5 and 6 of the benzimidazole nucleus, may form together the ring

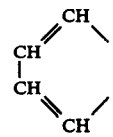

The compounds (I) possess interesting antihistaminic and anti-allergic activities.

8 Claims, No Drawings

PHARMACOLOGICALLY ACTIVE ALKYLTHIOBENZIMIDAZOLE DERIVATIVES AND PROCESS FOR THE PREPARATION THEREOF

The present invention refers to a new class of alkylthiobenzimidazole derivatives having an interesting antihistaminic and anti-allergic activities and to the process for the preparation thereof.

More particularly, the compounds of the present invention are represented by the class of compounds having the structure formula:

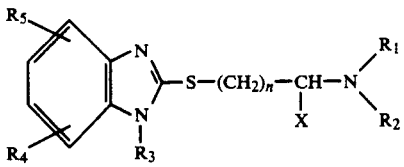

wherein
- $R_1$ and $R_2$ each represent a 1-3 carbon atom alkyl radical or they may form with the adjacent nitrogen atom, an optionally substituted heterocyclic ring, in particular an heterocyclic ring selected from the group consisting of optionally substituted pyrrolidine, piperidine, piperazine and morpholine
- X represents a hydrogen atom or methyl radical
- n is 1 or 2
- $R_3$ represents a 4-6 carbon atom alkoxyalkyl radical, a 7 or 8 carbon atom arylalkyl or a 5 or 6 carbon atom cycloalkyl with the exception that $R_3$ may not be an arylalkyl radical when $R_1$ and $R_2$ each represent a 1-3 carbon atom alkyl radical
- $R_4$ and $R_5$ may be the same or different and each represent a hydrogen atom or a 1-2 carbon atom alkyl or they, attached at the positions 5 and 6 of the benzimidazole nucleus, may form together the ring

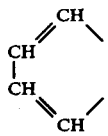

and by the corresponding non-toxic, pharmaceutically acceptable and suitable acid addition salts.

The compounds of formula (I) are easily prepared starting from 2-mercaptobenzimidazole, which may be substituted at the benzene ring, by first introducing the radical in position 2, by means of reaction in warm conditions, with the suitable aminoalkylhalide Hal—(CH$_2$)$_n$—CH(X)—NR$_1$R$_2$, wherein X, N,R$_1$ and R$_2$ have the above identified meanings and Hal is a halogen atom, preferably chlorine or bromine, then reacting in warm conditions the so obtained 2-thiosubstituted benzimidazole with the halide Hal—R$_3$, wherein Hal and R$_3$ have the above meanings.

The process may be schematically described as follows:

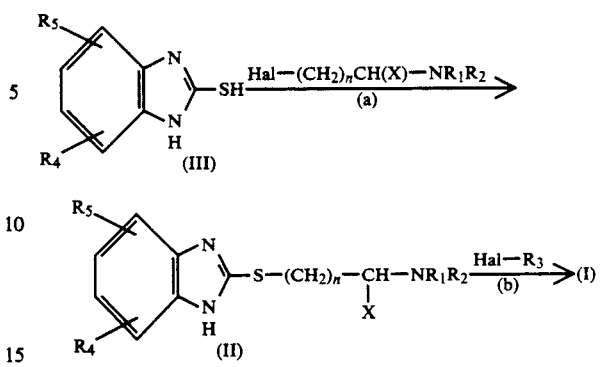

wherein $R_1$, $R_2$, X, n, $R_3$, $R_4$, $R_5$ and Hal have the above mentioned meanings.

Both the two reactions (a) and (b) are carried out in warm conditions, at a temperature between 50° and 140° C., in an alkaline medium, in suitable organic solvents. The reaction (a) preferably, is carried out in solvents consisting of lower alcohols, preferably ethyl alcohol, while reaction (b) preferably takes place in aprotic solvents, such as dioxane and N,N-dimethylformamide. Both the products (II) and (I), where possible, may be usefully isolated as non-toxic, pharmaceutically acceptable salts with suitable acids.

The anti-histaminic activity of the compounds of the invention has been evaluated studying either the effect on the mortality induced by histamine and the affinity towards H$_1$ histaminergic receptors. The tests were carried out according to the following methods.

EFFECT ON THE MORTALITY INDUCED BY HISTAMINE

The method described by Romer D. et al., (Med. Welt 17, 791, 1966) was followed and the tests were carried out on male albino guinea pigs (Dunkin-Hartley), weighing 350-450 g, which were kept in cages with a grid floor, on an empty stomach for 24 hrs and with water ad libitum.

The compounds (I) were dissolved in saline solution and intraperitoneally administered to the animals: 30 minutes later the same animals were intravenously treated with 1.25 mg/kg of histamine dihydrochloride in saline solution. The control animals, to which only the histamine solution had been administered, showed a 100% mortality during the first hour following the treatment.

It was evaluated ID$_{50}$ which corresponds to the amount of the compound able to inhibit 50% of the mortality induced by histamine: the estimation of ID$_{50}$ was carried out by applying the 'probit' method (Finney D. J. "Statistical Method in Biological Assay" p. 512, 1957).

EVALUATION OF THE AFFINITY TOWARDS H$_1$ HISTAMINERGIC RECEPTORS

The affinity of the examined compounds towards H$_1$ histaminergic receptors as evaluated by displacement curves which were obtained of different concentrations, against [$^3$H] Mepyramine in homogenates of rat brain "in toto", according to the method described by Trau et al. (Proc. Natl. Acad. Sci., 75, 6290–1978), with minor modifications.

The incubation was performed at 25° C. for 15 minutes, in a final volume of 1 ml of 50 nM Na/K phosphate buffer, pH 7.5, in the presence of 2 nM [$^3$H] Mepyramina and 1.5 mg of cerebral protein. Aspecific binding was defined as the residual radioactivity bound in the presence of 0.1 nM Clemastine. The test compounds were dissolved in phosphate buffer or dimethylsulfoxide (DMSO), the final concentration of DMSO was 0.5%. Incubation was terminated by filtration through glass fiber GF/B filters pre-soaked with 0.1% polyethylenimine (PEI). The radioactivity trapped by filters was counted by liquid scintillation.

Inhibition constant (Ki) was calculated by the method proposed by Cheng and Prusoff (Biochem. Pharmacol. 22, 3099–3108, 1973), from IC$_{50}$ values obtained by non-linear fitting analysis of displacement curves.

The anti-allergic activity of the compounds of the present invention has been evaluated studying the protection towards the mortality induced by administration of compound 48/80.

EFFECT ON THE MORTALITY INDUCED BY COMPOUND 48/80

The tests were carried out according to the method described by C. J. E. Niemergeers et al., Arch. Int. Pharmacodyn., 234,164,–1978. Sprague Dawley Nos male rats (Nossan, Correzzana, Milano) weighing 140–150 g, divided into groups of 10 animals each, on an empty stomach for 24 hrs and with water ad libitum, were kept in cages with a grid floor, then treated intravenously with 2 mg/kg of compound 48/80 (1 ml/rat). The compound (I) or the carrier were dissolved in water (5 ml/kg) and intraperitoneally administered to the animals 30 minutes before the treatment with the compound 48/80. The mortality occurred in the group of treated animals during the first 4 hours following the treatment was noted down. The results were expressed as the number of animals dead with respect to the number of treated animals.

The experimental data were submitted to the variance analysis and to the subsequent multiple comparisons according to Dunnett (D. J. Finney, "Statistical Method in Biological Assay", Ed. L. Griffin and Co., Ltd., pg. 152–157, Edition Ames, Iowa, 1971).

The Letal Dose$_{50}$ (LD$_{50}$) was evaluated on mice using Swiss Nos (Nossan, Correzzana, Milano) mice weighing 18–20 g each. The animals, divided into groups of 10 animals each (5M+5F), were on an empty stomach for 18 hrs, with water ad libitum, and kept in cages with a grid floor. The compounds (I) were dissolved in water or suspended in 0.5% carboxymethylcellulose and intraperitoneally administered to the animals (10 ml/kg). The mortality occurred in the tested animals within the following 6 hours was noted down. At the expiry of the 6th hour, the animals were allowed to eat up to the end of the experimentation which lasted 14 days. During this period all the toxic symptoms and the mortality occurring were noted.

The animals which died during the test period and those which were sacrificed at the end of the same, underwent autopsy for a macroscopic examination of their main organs. The experimental data were statistically compared with the X$^2$ method and LD$_{50}$ was extrapolated by the 'probit' method.

The data resulting from the tests carried out on some significant compounds of the class (I), are given in the following Table. The compounds were also tested as to the effect on the sleeping time and it was found that, at their active dose, they practically had no effect on the sleeping time.

| Compound | Histamine mortality ID$_{50}$ (μg/kg) i.p. | Compound 48/80 mortality ID$_{50}$ (μg/kg) i.p. | Sleeping time % increase 25 mg/kg i.p. | Acute toxicity LD$_{50}$ (mg/kg) i.p. | H$_1$-receptor binding IC$_{50}$ (nM) |
|---|---|---|---|---|---|
| Example 3 | 10.9 (5.5–21.6) | 8 (4–15) | 5 | >100 | 2.4 |
| Example 5 | 50 (19–131) | 9 (5–17) | 10 | ~100 | 6.1 |
| Terfenadine | 735 (437–1237) | 1990 (1080–3720) | 8 | >100 | 283.1 |

For therapeutic administration, the compounds according to the present invention are used in the form of pharmaceutical preparation which contain said compounds in admixture with pharmaceutically acceptable carriers such as an organic or inorganic solid or liquid excipient suitable for oral or parenteral administration. The compounds of the invention may be contained in these pharmaceutical preparations in the form of free base of in the form of their non-toxic acid addition salts. The inorganic acids which may be employed to prepare these acid addition salts may be, for example, hydrochloric or sulphuric acid. The organic acids which may be employed are, for example, maleic, citric, fumaric and succinic acid. The pharmaceutical preparations may be in solid form as capsules, tablets, dragees or in liquid form such as solutions, suspensions or emulsion. If desired, there may be included in the above preparations auxiliary substances such as stabilizing agent and other commonly used additives, or there may be contained other therapeutically active agents suitable to be administered together with the compounds of the invention. The dosage of the compounds will vary from the administration route and will also depend upon the age and condition of the patient.

The following Examples are given by way of better illustrating the invention, but without limiting it.

EXAMPLE 1

1-Benzyl-2-[2-(4methylpiperazin-1-yl) ethylthio]benzimidazole

Grams 2.2 2-mercapto-1H-benzimidazol and 2.4 g NaOH were dissolved in 40 ml 90% ethyl alcohol, then 3.5 g 1-(2-chloroethyl)-4-methylpiperazine hydrochloride were added thereto. The reaction mixture was refluxed for 2 hours, the solid precipitate removed by filtration, the limpid solution evaporated to dryness and the residue dissolved in chloroform and washed with water. The organic phase was made anhydrous, then evaporated to dryness and the residue chromatographed on a column eluting with chloroform, methyl alcohol, cyclohexane, ammonium hydroxide (68:15:15:0.2). The fractions which contained the product, were collected together and evaporated to dryness and the residue which was triturated with isopropyl ether, gave 0.65 g 2-[2-(4-methylpiperazin-1-yl)ethylthio] benzimidazole melting at 93°–95° C. (with a slight decomposition).

Grams 2 2-[2-(4-methylpiperazin-1-yl)ethylthio] benzimidazole, 0.86 ml benzyl chloride, a 3.5 g aqueous solution containing 1.16 g NaOH and 7.5 ml N,N-dimethylformanide were refluxed for 6 hours, then the solid precipitate was filtered off, and the limpid solution was evaporated almost to dryness. The obtained residue was dissolved in chloroform and water and the extraction was carried out three times; the organic phase was washed, made anhydrous and then evaporated to dryness. The obtained residue was chromatographed on a column eluting with chloroform, methyl alcohol, cyclohexane, ammonium hydroxide (65:15:15:0.1). The fractions, which contained the compound, were evaporated to dryness and the residue which was taken up with boiling petroleum ether (80°–$\phi$° C.) and separated from the insoluble oil, gave, on cooling 0.3 g 1-benzyl-2-[2-4-methylpiperazin-1-ethylthio]benzimidazole melting at 122°–125° C.

EXAMPLES 2–12

Operation was carried out in a manner similar to the above Example and the following compounds were prepared:

1-Benzyl-2-[2-[4-(4-chlorobenzhydryl)piperazin-1-yl]ethylthio]benzimidazole, as an oil, starting from 2-[2-[4-(4-chlorobenzhydryl) piperazin-1-yl] ethylthio]-benzimidazole (m.p. 96°–98° C., with decomposition) and benzyl chloride.

1-(2-Ethoxyethyl)-2-(2-dimethylaminoethylthio)benzimidazole. 2 HCl, (m.p. 159°–161° C.) starting from 2-(dimethylaminoethylthio)benzimidazole and 2-ethoxyethyl chloride.

1-(2-Ethoxyethyl)-2-(3-dimethylaminopropylthio)benzimidazole, as a straw colored oil, starting from 2-(3-dimethylaminopropylthio)benzimidazole (m.p. 77°–79° C.) and 2-ethoxyethyl chloride.

1-(2-Ethoxyethyl)-2-(2-dimethylaminoisopropylthio)-benzimidazole, starting from 2-(2-dimethylaminoisopropylthio)benzimidazole, (m.p. 166°–169° C.) and 2-ethoxyethyl chloride.

1-(2-Ethoxyethyl)-2-(2-piperidin-1-ylethylthio)benzimidazole starting from 2-(2-piperidin-1-ylethylthio)benzimidazole, (m.p. 141°–142° C.) and 2-ethoxyethyl chloride.

1-(2-Ethoxyethyl)-2-[2-(N-morpholino)ethylthio]benzimidazole, as an oil (Rf (CHCl$_3$, CH$_3$OH 7.3)=0.82) starting from 2-(2-N-morpholino)ethylthio benzimidazole (m.p. 118°–119° C.) and 2-ethoxyethyl chloride.

1-(2-Ethoxyethyl)-2-(2-pyrrolidin-1-ylethylthio)benzimidazole, starting from 2-(2-pyrrolidin-1-ylethylthio)benzimidaxole, (m.p. 116°–117° C.) and 2-ethoxyethyl chloride.

1-Cyclopentyl-2-dimethylaminoethylthio)benzimidazole, as an oil, starting from 2-(2-dimethylaminoethylthio)benzimidazole and cyclopentyl bromide.

1-(2-Ethoxyethyl)-2-(2-dimethylaminoethylthio)-5,6-dimethyl benzimidazole, as an oil, |Rf (CHCl$_3$, CH$_3$OH 7:3)=0.62|, starting from 5,6-dimethyl-2-(2-dimethylaminoethylthio)benzimidazole (m.p. 103°–104° C.) and 2-ethoxyethyl chloride.

1-(2-Ethoxyethyl)-2-(2-diethylaminoethylthio)benzimidazole starting from 2-(2-diethylaminoethylthio)-benzimidazole (m.p. 104°–105° C.) and 2-ethoxyethyl chloride.

1-(2-Ethoxyethyl)-2-(2-dimethylaminoethylthio)naphthoimidazole starting from 2-(2-dimethylaminoethylthio)naphthoimidazole (m.p. 165°–167° C.) and 2-ethoxyethyl chloride.

What we claim is:

1. An alkylthiobenzimidazole derivative having the structural formula:

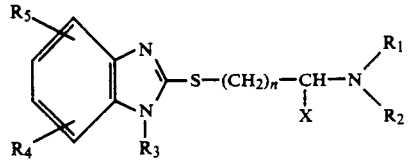

wherein R$_1$ and R$_2$ each represent 1–3 carbon alkyl or they may form together with the adjacent nitrogen, an optionally substituted heterocyclic ring selected from the group consisting of pyrrolidine, piperidine, piperazine and morpholine; X represents hydrogen or methyl; n is 1 or 2; R$_3$ represents 4–6 carbon alkoxyalkyl, or 5 or 6 carbon cycloalkyl ; and R$_4$ and R$_5$ may be the same or different and each represent hydrogen or 1 or 2 carbon alkyl or they, attached at the positions 5 and 6 of the benzimidazole nucleus, may form together the ring

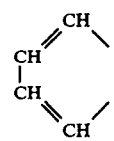

or a pharmaceutically acceptable, suitable acid addition salt thereof.

2. The alkylthiobenzimidazole derivative according to claim 1, wherein R$_3$ represents 2-ethoxyethyl.

3. 1-(2-Ethoxyethyl)-2-(2-dimethylaminoethylthio)-benzimidazole.

4. 1-(2-Ethoxyethyl)-2-(2-dimethylaminoisopropylthio)benzimidazole.

5. An antihistamine and/or anti allergic composition which comprises an antihistaminically and/or antiallergically effective amount of a compound of claim 1 in an admixture with a suitable pharmaceutically acceptable diluent.

6. An antihistamine and/or antiallergic compositions which comprises an antihistaminically and/or antiallergically effective amount of a compound of claim 2 in admixture with a suitable pharmaceutically acceptable diluent.

7. An antihistamine and/or antiallergic composition which comprises an antihistaminically and/or antiallergically effective amount of a compound of claim 3 in admixture with a suitable pharmaceutically acceptable diluent.

8. An antihistamine and/or antiallergic composition which comprises an antihistaminically and/or antiallergically effective amount of a compound of claim 4 in admixture with a suitable pharmaceutically acceptable diluent.

* * * * *

UNITED STATES PATENT AND TRADEMARK OFFICE
CERTIFICATE OF CORRECTION

PATENT NO. : 4,983,620

DATED : JANUARY 8, 1991

INVENTOR(S) : ROBERTO P. GIANI ET AL

It is certified that error appears in the above-identified patent and that said Letters Patent is hereby corrected as shown below:

Column 1, line 60, change "N,$R_1$" to -- n,$R_1$ --.

Column 4, line 35, change "base of" to -- base or --.

Column 5, lines 21-22, change "1-benzyl-2-[2-4-methylpiperazin-1- ethylthio]benzimidazole" to

-- 1-benzyl-2-[2-(4-methylpiperazin-1-yl)-ethylthio]benzimidazole --.

Signed and Sealed this

Nineteenth Day of May, 1992

*Attest:*

DOUGLAS B. COMER

*Attesting Officer*  *Acting Commissioner of Patents and Trademarks*